US005662475A

United States Patent [19]
Mena

[11] Patent Number: 5,662,475
[45] Date of Patent: Sep. 2, 1997

[54] UNIVERSAL PROSTHETIC AND IMPLANT ABUTMENT

[76] Inventor: Raul R. Mena, 201 N. University Dr., Suite 101, Plantation, Fla. 33324

[21] Appl. No.: 612,699

[22] Filed: Mar. 8, 1996

[51] Int. Cl.$^6$ .................... A61C 13/12; A61C 13/225; A61C 8/00
[52] U.S. Cl. .................................... 433/172; 433/174
[58] Field of Search .................... 433/172, 173, 433/174, 175, 176, 177

[56] References Cited

U.S. PATENT DOCUMENTS

| | | | |
|---|---|---|---|
| 4,713,004 | 12/1987 | Linkow et al. | 433/174 |
| 4,793,808 | 12/1988 | Kirsch | 433/173 |
| 4,832,601 | 5/1989 | Linden | 433/173 |
| 4,907,969 | 3/1990 | Ward | 433/173 |
| 5,302,125 | 4/1994 | Kownacki et al. | 433/172 |
| 5,480,304 | 1/1996 | Nardi | 433/172 |

*Primary Examiner*—Nicholas D. Lucchesi
*Attorney, Agent, or Firm*—J. Sanchelima

[57] ABSTRACT

A device for supporting a dental prosthesis and to provide a rigid engagement to a dental implant or natural dentition while correcting the lack of parallelism of the latter. The device includes an implant abutment that has a spherical portion and an anchorage portion for rigidly mounting to the implant. A tubular engaging assembly supports the prosthesis and includes two ends. At least one of the ends has a diameter that is smaller than the diameter of the spherical portion and sufficiently large to house a substantial area of the spherical portion. A dental surgeon fills the tubular engaging assembly with cement and brings it in contact with the spherical portion. A protuberance with irregularities for enhancing the engagement is introduced in side the tubular engaging assembly. The latter can be positioned in site to correct any lack of parallelism of the implant.

16 Claims, 6 Drawing Sheets

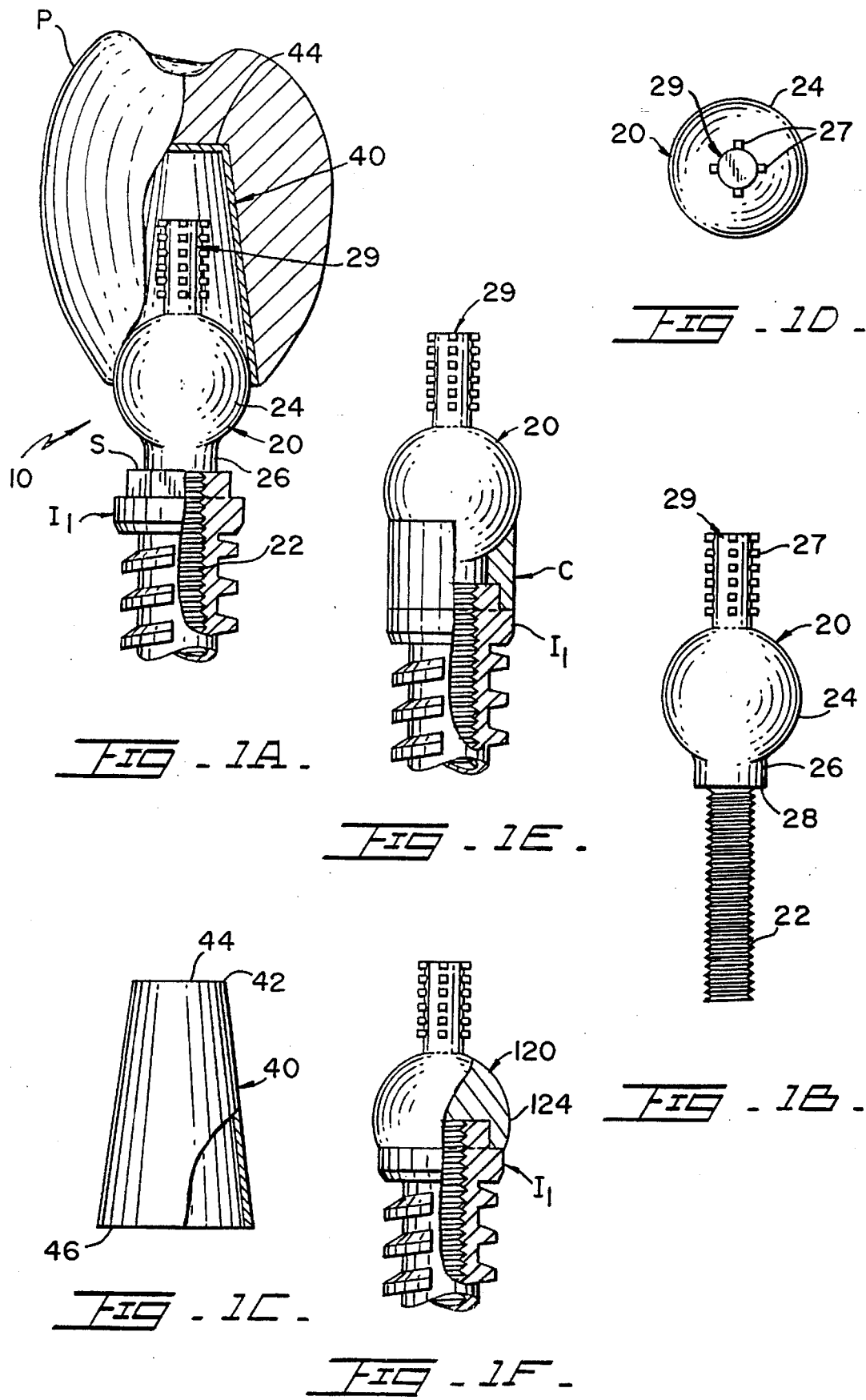

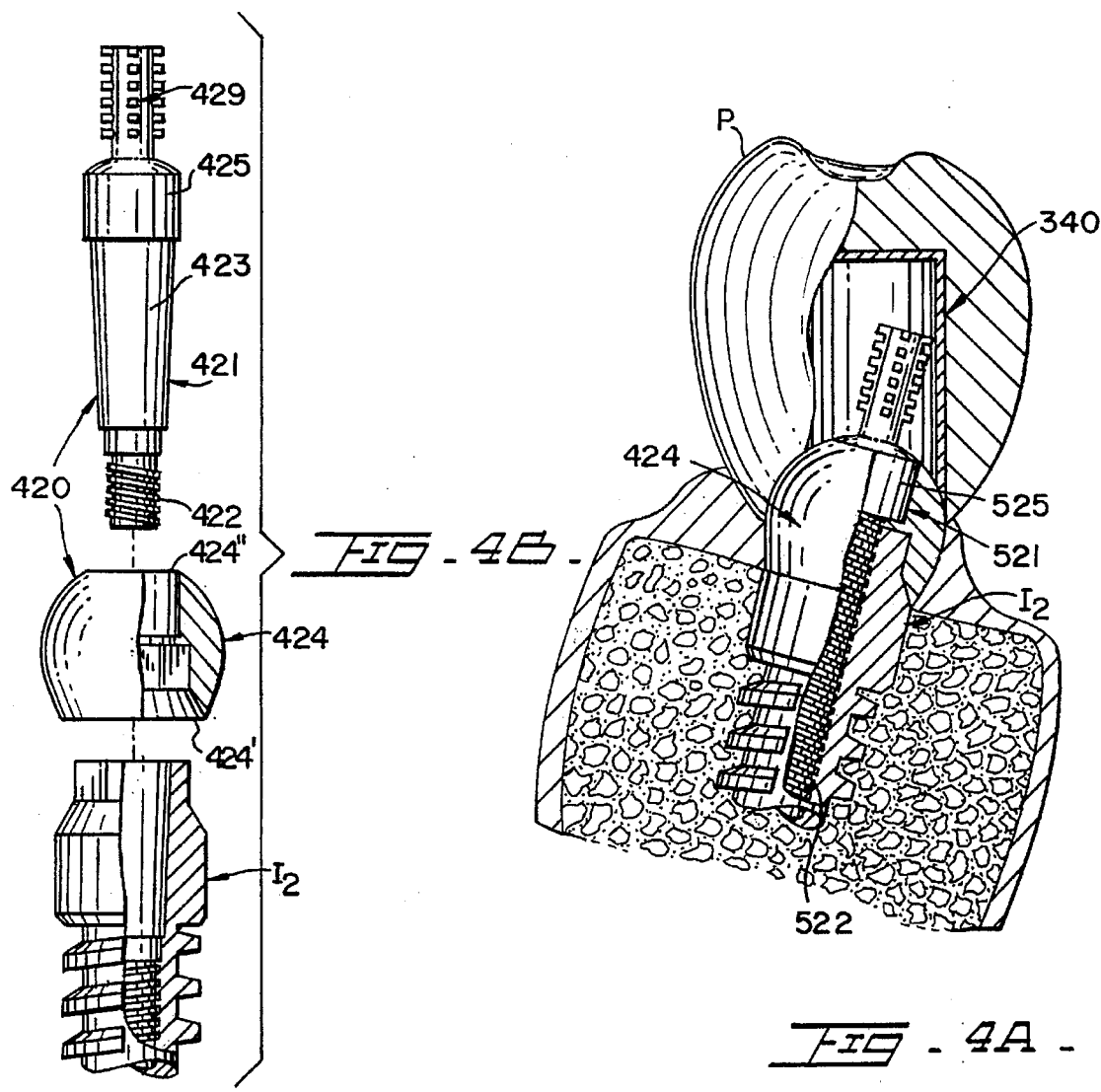

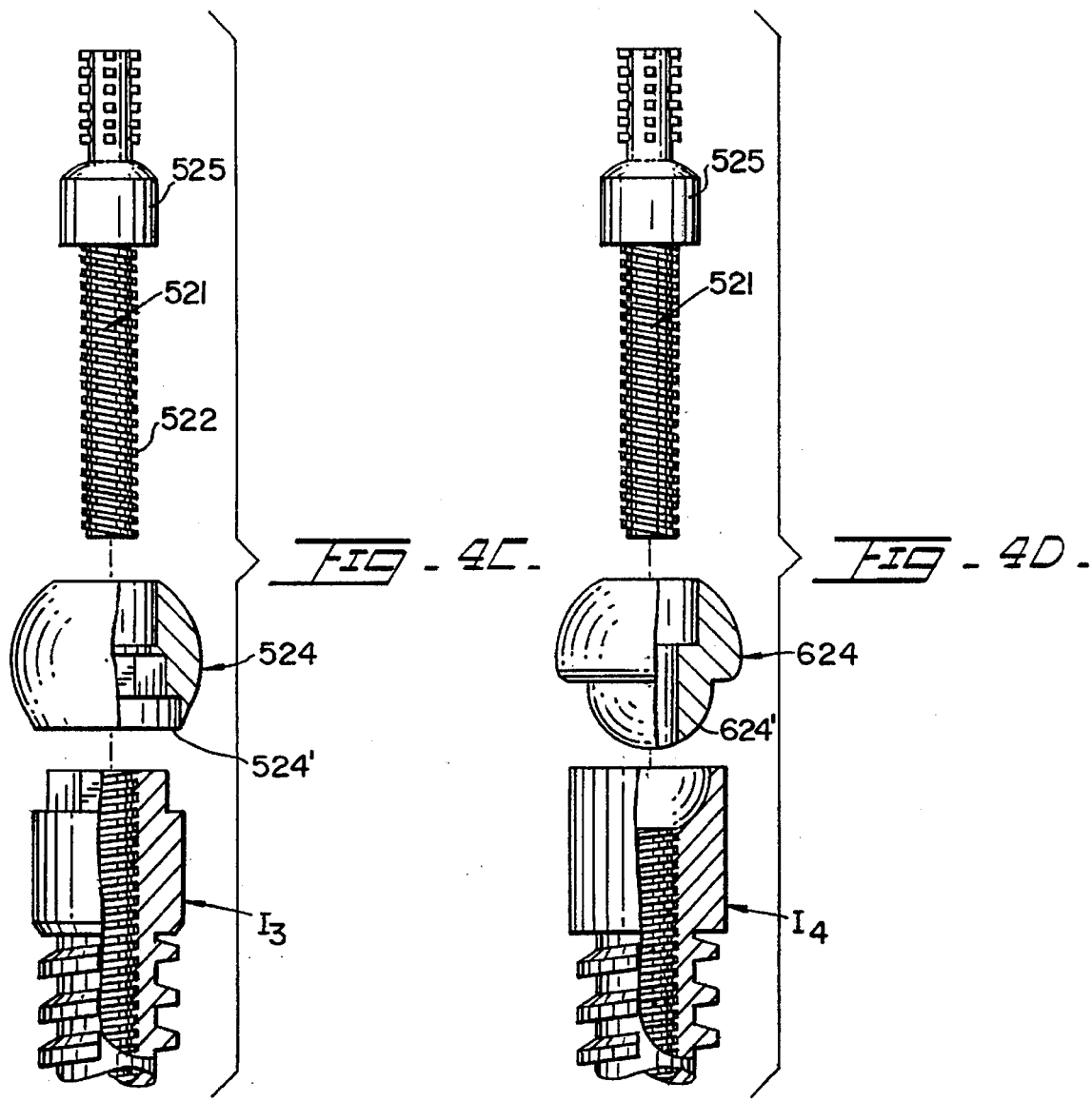

UNIVERSAL PROSTHETIC AND IMPLANT ABUTMENT

BACKGROUND OF THE INVENTION

1. Field of the Invention

The present invention relates to dental abutments, and more particularly, to the type that can be readily used with most implants available today.

2. Description of the Related Art

Many types of dental abutments have been designed in the past. These abutments are designed to correct the lack of parallelism that typically results when dental implants are secured to a patient's jaw. One approach has been to develop a line of abutments designed to correct the lack of parallelism over a predetermined range of angles. This approach, however, required a considerable invention and for a predetermined number of correction of angles.

None of these devices, however, provide for an abutment that can be readily conformed to correct the lack of parallelism by merely positioning a prosthetic engagement assembly over the spherical portion of an implant abutment assembly. This approach gives a dental surgeon a wide range of angles for positioning the prosthetic engagement assembly and, more important, he or she can position it on site with minimum discomfort to the patient.

SUMMARY OF THE INVENTION

It is one of the primary objects of the present invention to provide a universal abutment for correcting lack of parallelism in dental implants, and/or natural dentition.

It is another object of the present invention to provide an abutment device that can be continuously adjusted over a predetermined range of angles to correct said lack of parallelism.

Still another object of the invention is to provide an abutment device that can be positioned in site with minimum discomfort to the patient.

Yet another object of this invention is to provide an abutment that is compatible with the majority of implants available today and permits the use of pre-manufactured tubular base for a prosthesis, or even a pre-manufactured prosthesis.

It is yet another object of this invention to provide such a device that is inexpensive to manufacture and maintain while retaining its effectiveness.

Further objects of the invention will be brought out in the following part of the specification, wherein detailed description is for the purpose of fully disclosing the invention without placing limitations thereon.

BRIEF DESCRIPTION OF THE DRAWINGS

With the above and other related objects in view, the invention consists in the details of construction and combination of parts as will be more fully understood from the following description, when read in conjunction with the accompanying drawings in which:

FIG. 1A represents a elevational view, with a partial cross-section, of one of the preferred embodiments for an abutment incorporating the teachings of the present invention as it is used with one type of conventional dental implant $I_1$.

FIG. 1B is an elevational view of the abutment engaging assembly used in FIG. 1A.

FIG. 1C shows an elevational view, with a partial cross-section of the prosthetic engagement assembly used in FIG. 1A.

FIG. 1D is a top view of the abutment engaging assembly shown in FIG. 1B.

FIG. 1E shows the abutment engaging assembly used in FIG. 1A with implant $I_1$ and casing C.

FIG. 1F shows dental implant $I_1$ with a modified version of the implant abutment assembly used in FIG. 1A.

FIG. 4A shows an elevational side view of a portion of implant $I_2$ mounted at an angle in a patient's jaw bone, with a modified version of the implant abutment consisting of two parts, and a fourth alternate embodiment for the plain cylindrical prosthetic engagement assembly.

FIG. 4B is an elevational exploded view, with a partial cross-section of a portion of implant $I_2$, with another modified version of the implant abutment and a third alternate embodiment for the prosthetic engagement assembly.

FIG. 4C is an elevational exploded view with a partial cross-section of a portion of implant $I_3$ and another alternate embodiment of the implant abutment engaging assembly.

FIG. 4D is an elevational exploded view with a partial cross-section of a portion of implant $I_4$ and another alternate embodiment of the implant abutment engaging assembly.

DETAILED DESCRIPTION OF THE PREFERRED EMBODIMENT

Figure 2A:
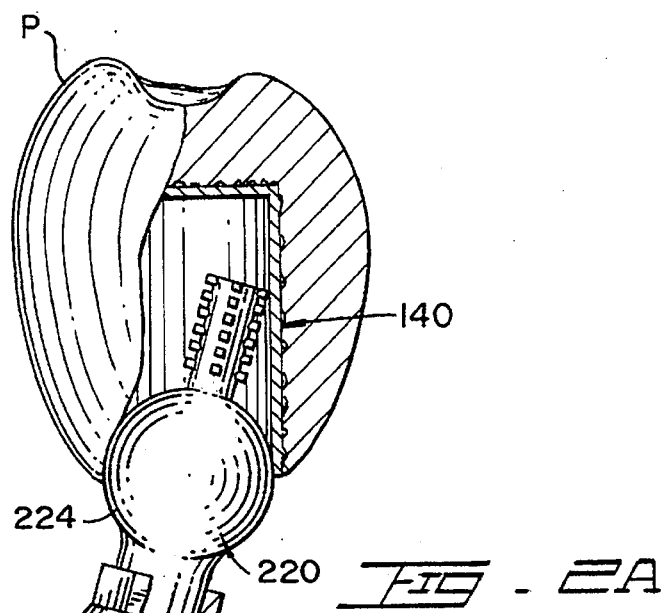
FIG. 2A represents an elevational view, with a partial cross-section of an alternate embodiment for the prosthetic engagement assembly of the cylindrical type, and implant $I_2$ at an angle.
Figure 2B:
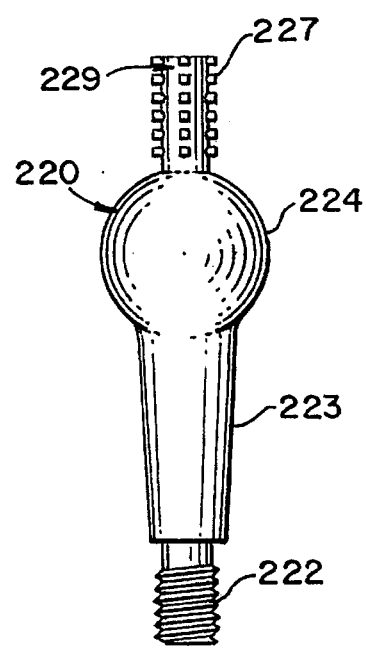
FIG. 2B shows an elevational view of the implant abutment assembly used in FIG. 2A.
Figure 2C:
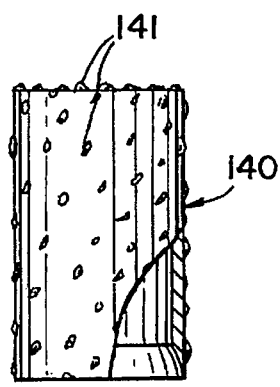
FIG. 2C is a elevational view with a partial cross section of the prosthetic engagement assembly used in FIG. 2A.

Referring now to FIG. 1, where the preferred embodiment for the present invention is generally referred to with numeral 10, it can be observed that it basically includes implant abutment assembly 20 (and other modified versions ending with the numeral 20 in the different drawings) and prosthetic engagement assembly 40 (and other embodiments referenced with numeral that end with 40 in the different drawings). These two assemblies provide the necessary engagement interface for prosthesis P and implant I (different subscripts denoting different types of implants with which the present invention is compatible).

Referring now to FIG. 1A, it can be observed that implant $I_1$ cooperatively receives threaded end 22 of implant abutment assembly 20. Assembly 20 includes spherical portion 24 that is rigidly mounted to threaded end 22 through skirt 26, as best seen in FIGS. 1A and 1B. Skirt 26 includes a flat lower edge 28 that comes in cooperative abutment with upper surface S of implant $I_1$. Anchorage protuberance 29 is mounted to spherical portion 24, opposite to skirt 26. In the preferred embodiment, protuberance 29 is an elongated member coaxially disposed with respect to threaded end 22.

Prosthetic engagement assembly 40 has a frustroconical shape, in one of the preferred embodiments, as shown in FIG. 1C. Narrower end 42 of assembly 40 may include top wall 44, as best seen in FIGS. 1A and 1C. Wider end 46 has a diameter that is smaller than the diameter of spherical portion 24 but large enough so that a substantial portion of the latter can be housed within assembly 40 when the later is brought in contact with the former, as shown in FIG. 1A. A dental surgeon will thus be allowed to fill the interior of assembly 40 with a cement substance, bringing assembly 40 in contact with portion 24 enclosing protuberance 29. To correct any lack of parallelism, the surgeon merely has to move assembly 40 until the proper position is achieved. Protuberance 29 is provided with irregularities 27 that enhance its adherence to the cement, as shown in FIGS. 1A; 1B and 1D. In FIG. 1E, implant $I_1$ is illustrated engaged with casing C. Casing C prevents a patient's jaw bone from storing food rests in the cavity formed between prosthesis P and surface S of implant $I_1$.

In FIG. 1F, an alternate embodiment of abutment 20 is illustrated. Implant abutment assembly 120 includes semi-spherical portion 124 that has a such internal structure that permits the latter to engage with upper surface S of implant $I_1$ without using casing C, shown in FIG. 1E, thereby enhancing the same hygienic propose.

In FIG. 2A, another implant type $I_2$ is illustrated, at an angle with respect to prosthesis P, after the lack of parallelism has been corrected with the proper positioning of prosthetic engagement assembly 240. Here, implant abutment assembly 220 is similar to implant abutment 20 with the exception of its threaded end 222 that is now separated from spherical portion 224 by tapered member 223. There is no skirt in this version and the engagement is different, as seen in FIG. 2A. However, the engagement function of this part of assembly 220 with a prosthetic engagement assembly (40; 140; 240 or other) is the same. The same can be said about anchorage protuberance 229 and irregularities 227. The alternate embodiment for prosthetic engagement assembly 140 shows a cylindrical body that provides more latitude in the range of the positions that the surgeon will have. This can be readily seen in FIG. 2A. Irregularities 141 are intended to enhance the engagement of prosthesis P with prosthetic engagement assembly 140. The function of assemblies 220 and 140 is basically the same, allowing a surgeon to rotate or position assembly 140, in site, to correct the lack of parallelism of an implant.

Figure 3A:
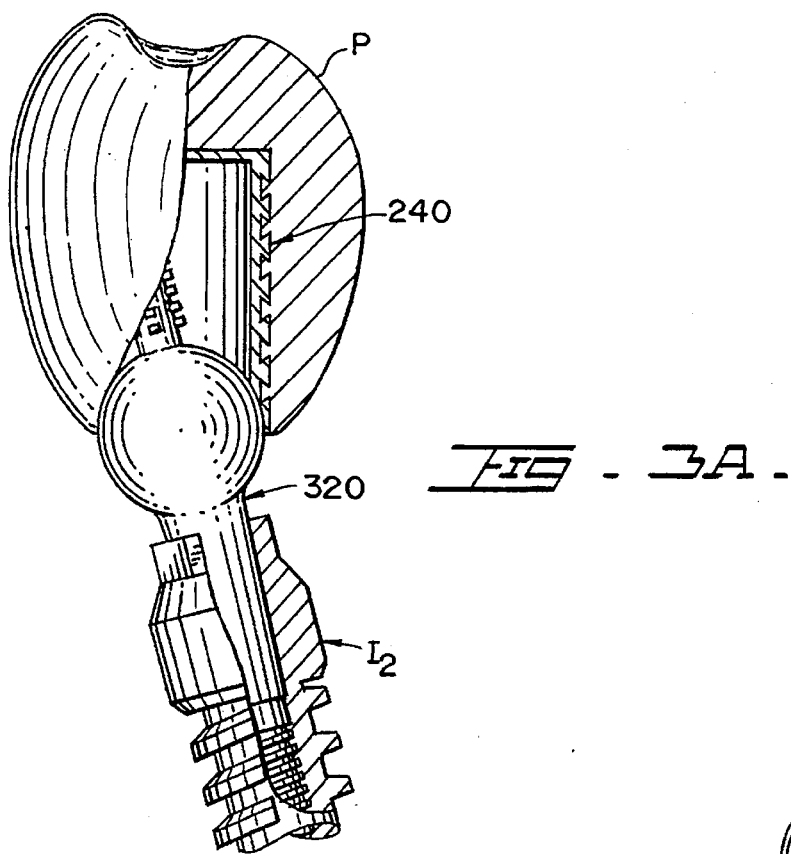
FIG. 3A represents a elevational view, with a partial cross-section of a second alternate embodiment for a prosthetic engagement assembly and a modified implant abutment assembly.
Figure 3B:
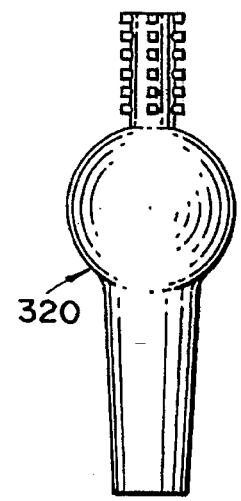
FIG. 3B shows an elevational side view of the implant abutment assembly used in FIG. 3A.
Figure 3C:
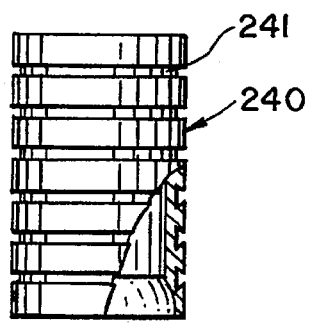
FIG. 3C is a elevational view with a partial cross section of the prosthetic engagement assembly used in FIG. 3A.

Similarly, in FIGS. 3A; and 3B a modified version of implant abutment assembly 320 is shown wherein the threaded end is missing. The mounting of assembly 320 is accomplished by cementing it to the central opening of implant $I_2$. Prosthetic engagement assembly 240 has a cylindrical shape with peripheral slots 241 intended, like irregularities 141, to enhance the engagement between prosthesis P and assembly 240, when the latter's interior is filled with cement.

In FIG. 4B, a different version of implant abutment 420 is shown and it includes two separate parts that cooperatively mate with implant $I_2$. One of these parts corresponds to post member 421 and the other one to spherical portion 424. Post member 421, as is shown in FIG. 4B, includes anchorage protuberance 429, base portion 425, tapered member 423 and threaded end 422. Spherical portion 424 includes a through opening with frustroconical lower end 424' and cylindrical upper end 424". Lower end 424' of the through opening has a termination that matingly engages with the exposed end of implant $I_2$ at the end of the beveled portion. Upper end 424" has cooperative dimensions to snugly receive base portion 425.

Other variations of post members are shown in FIGS. 4A; 4C and 4D. In FIG. 4A, the assembly combination is illustrated, wherein cylindrical prosthesis engagement assembly 340 with a plain outer surface can also be used. The important function being the cooperative engagement that allows the surgeon to readily position assembly 340 and prosthesis P in place. Post member 521 includes threaded end 522 and base portion 525, and the tapered portion has been eliminated. In FIG. 4C, a modified version of spherical portion 524 is shown with a cylindrical inner end 524', which in turn is snugly mounted onto the uppermost flange of implant $I_3$. In FIG. 4D, a modified version of spherical portion 624 is shown with a convex end 624' in cooperative mating engagement with implant $I_4$.

Figure 5A:
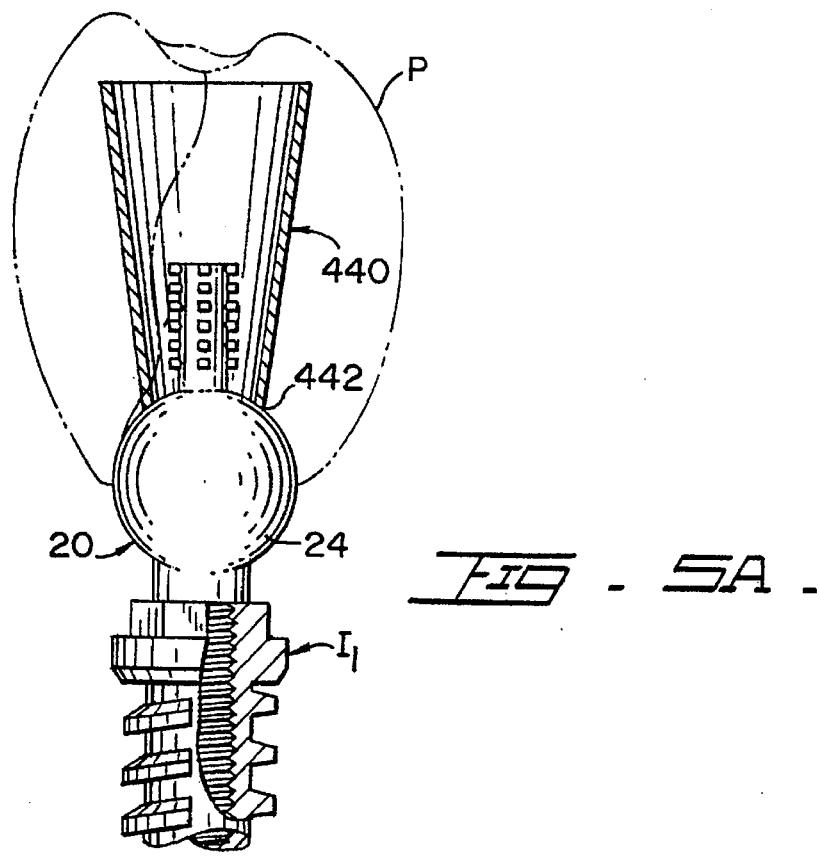
FIG. 5A represents a elevational view, with a partial cross-section, of the implant abutment assembly and implant $I_1$ shown in FIG. 1A, but with the frustroconical prosthetic engagement assembly in reverse manner.
Figure 5B:
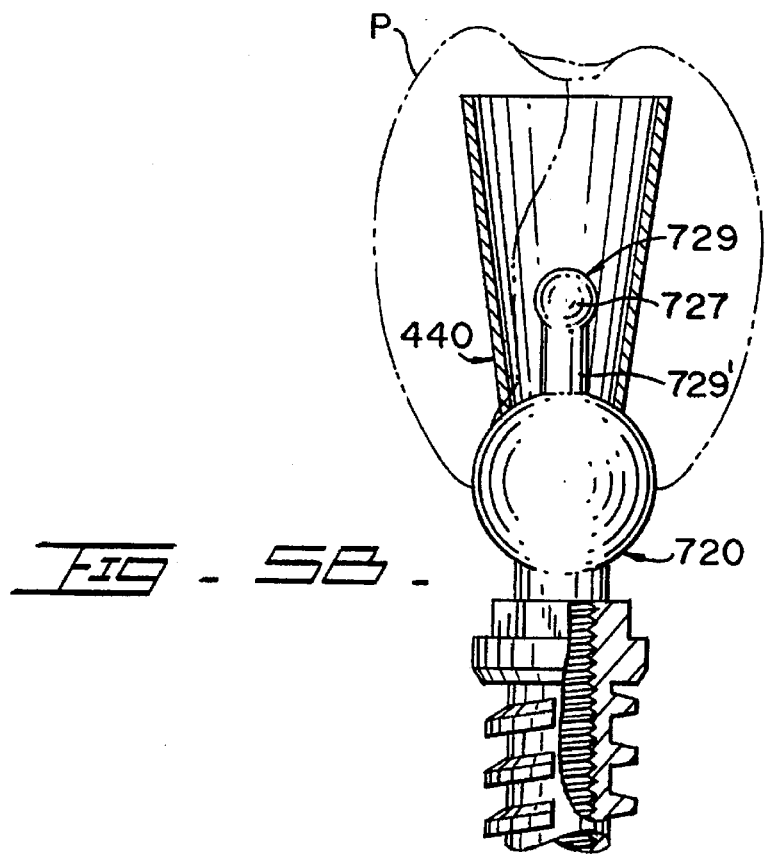
FIG. 5B shows the previous figure but with another alternate embodiment of implant abutment assembly.

FIGS. 5A and 5B show a different prosthesis engagement assembly 440 corresponding to an inverted assembly 40 shown in FIG. 1A. Basically, narrower end 442 comes in contact with spherical portion 24 of implant abutment 20. While sacrificing part of the interface area available for the cementation bond, the surgeon will have even more latitude in moving assembly 440 about in his or her attempt to correct the lack of parallelism.

In FIG. 5B, another alternate embodiment of implant abutment assembly 720 is illustrated. Anchorage protuberance 729 comprises elongated tubular member 729' with spherical termination 727 at its uppermost end. This spherical termination 727 permits a user to separate assembly 720 from any prosthetic engagement assemblies (40; 140; 240; 340 or 440) described above, without any difficulties.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. A device for supporting a dental prosthesis and providing a rigid engagement to dental implants or natural dentition, comprising:

A) abutment means having a spherical portion and anchorage means for mounting said abutment means to a dental implant or natural dentition;

B) tubular engaging means for supporting a dental prosthesis having first and second ends and said tubular engaging means having an internal diameter that is smaller than the diameter, throughout said tubular engaging means, of said spherical portion and housing part of said spherical portion; and C) means for securing said tubular engaging means to said part of said spherical portion housed by said tubular engaging means.

2. The device set forth in claim 1 wherein said abutment means includes a retention protuberance mounted on said spherical portion opposite to said anchorage means.

3. The device set forth in claim 2 wherein said first end of said tubular engaging means has a diameter that is slightly smaller than the diameter of said spherical portion.

4. The device set forth in claim 3 wherein said protuberance includes irregularity means for enhancing its engagement to said tubular engaging means.

5. The device set forth in claim 4 wherein said tubular engaging means has a uniform circular cross-section.

6. The device set forth in claim 5 wherein said tubular engaging means includes irregularity means for enhancing its engagement to said prosthesis.

7. The device set forth in claim 6 wherein said anchorage means includes an elongated threaded member that is cooperatively receivable by said implant.

8. The device set forth in claim 6 wherein said anchorage means includes a tapered end for cooperative engagement with said implant.

9. The device set forth in claim 4 wherein said tubular engaging means has a frustroconical shape with its larger diameter end in contact with said spherical portion.

10. The device set forth in claim 9 wherein said tubular engaging means includes irregularity means for enhancing its engagement to said prosthesis.

11. The device set forth in claim 10 wherein said anchorage means includes an elongated threaded member that is cooperatively receivable by said implant.

12. The device set forth in claim 11 wherein said anchorage means includes a tapered end for cooperative engagement with said implant.

13. The device set forth in claim 4 wherein said tubular engaging means has a frustroconical shape with its smaller diameter end in contact with said spherical position.

14. The device set forth in claim 13 wherein said tubular engaging means includes irregularity means for enhancing its engagement to said prosthesis.

15. The device set forth in claim 14 wherein said anchorage means includes an elongated threaded member that is cooperatively receivable by said implant.

16. The device set forth in claim 15 wherein said anchorage means includes a tapered end for cooperative engagement with said implant.

\* \* \* \* \*